US00PP17540P2

(12) United States Plant Patent
Parthasarathy et al.

(10) Patent No.: US PP17,540 P2
(45) Date of Patent: Mar. 27, 2007

(54) ***AGLAONEMA* PLANT NAMED 'CALYPSO'**

(50) Latin Name: *Aglaonema hybrida*
Varietal Denomination: Calypso

(76) Inventors: Gopalaswamy Parthasarathy, "Srinivasa", 237/46, Fifth Main Road, Chamrajpet, Bangalore 560018 (IN); Parthasarathy Mukundan, "Srinivasa", 237/46, Fifth Main Road, Chamrajpet, Bangalore 560018 (IN)

( * ) Notice: Subject to any disclaimer, the term of this patent is extended or adjusted under 35 U.S.C. 154(b) by 38 days.

(21) Appl. No.: 11/174,975

(22) Filed: Jul. 5, 2005

(51) Int. Cl.
*A01H 5/00* (2006.01)

(52) U.S. Cl. ..... Plt./376

(58) Field of Classification Search ..... Plt./376
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Aglaonema* plant named 'Calypso', characterized by its upright and outwardly arching plant form; vigorous growth habit; freely clumping habit; full, dense and bushy appearance; large glossy and twisting oblong leaves with acuminate apices; upper leaf surfaces dark green in color with gray green-colored chevrons interspersed with distinct golden yellow spots and blotches; lower leaf surfaces pale green in color with ivory white-colored midrib, spots and splashes; pale yellow to ivory white-colored leaf petioles; petiole wings with sparse and random green-colored spots; and tolerance to low temperatures.

1 Drawing Sheet

Botanical designation: *Aglaonema hybrida.*
Cultivar denomination: 'Calypso'.

BACKGROUND OF THE INVENTION

The present Invention relates to a new and distinct cultivar of *Aglaonema* plant, botanically known as *Aglaonema hybrida* and hereinafter referred to by the name 'Calypso'.

The new *Aglaonema* is the result of a planned breeding program conducted by the Inventors in Chamrajpet, Bangalore, India. The objective of the breeding program is to create new vigorous *Aglaonema* cultivars with compact and dense plant habit, unique leaf coloration, interesting leaf shapes, resistance to pathogens and pests common to *Aglaonemas* and tolerance to low temperatures.

The new *Aglaonema* originated from a cross-pollination made by the Inventors on Sep. 9, 1988 of a proprietary selection of *Aglaonema hybrida* identified as code number KSG 86-28, not patented, as the female, or seed, parent with an unnamed selection of *Aglaonema tricolor* (Nicolson) Jervis, not patented, as the male, or pollen, parent. The new *Aglaonema* was discovered and selected by the Inventors in 1989 as a single plant within the progeny of the stated cross-pollination in a controlled environment in Chamrajpet, Bangalore, India. The new *Aglaonema* was selected on the basis of its plant habit, leaf shape and uniquely colored foliage.

Asexual propagation of the new cultivar by divisions and cuttings since September, 1990 in a controlled environment in Chamrajpet, Bangalore, India, has shown that the unique features of this new *Aglaonema* are stable and reproduced true to type in successive generations.

SUMMARY OF THE INVENTION

The following traits have been repeatedly observed and are determined to be the unique characteristics of 'Calypso'.

These characteristics in combination distinguish 'Calypso' as a new and distinct cultivar of *Aglaonema:*

1. Upright and outwardly arching plant form.
2. Vigorous growth habit.
3. Freely clumping habit; full, dense and bushy appearance.
4. Large glossy and twisting oblong leaves with acuminate apices.
5. Unique leaf coloration; upper leaf surfaces dark green in color with gray green-colored chevrons interspersed with distinct golden yellow spots and blotches; lower leaf surfaces pale green in color with ivory white-colored midrib, spots and splashes.
6. Pale yellow to ivory white-colored leaf petioles; petiole wings with sparse and random green-colored spots.
7. Tolerant to low temperatures.

In side-by-side comparisons conducted by the Inventors in Chamrajpet, Bangalore, India, plants of the new *Aglaonema* differed from plants of the female parent selection in the following characteristics:

1. Plants of the new *Aglaonema* were more freely clumping than plants of the female parent selection.
2. Leaves of plants of the new *Aglaonema* were broader than leaves of plants of the female parent selection.
3. Plants of the new *Aglaonema* and the female parent selection differed in leaf and leaf petiole coloration.

In side-by-side comparisons conducted by the Inventors in Chamrajpet, Bangalore, India, plants of the new *Aglaonema* differed from plants of the male parent selection in the following characteristics:

1. Plants of the new *Aglaonema* were more freely clumping than plants of the male parent selection.
2. Leaves of plants of the new *Aglaonema* were broader than leaves of plants of the male parent selection.
3. Plants of the new *Aglaonema* and the male parent selection differed in leaf and leaf petiole coloration.

Plants of the new *Aglaonema* can be compared to plants of the cultivar Camouflage, disclosed in U.S. Plant Pat. No. 13,573. In side-by-side comparisons conducted in Chamrajpet, Bangalore, India, plants of the new *Aglaonema* differed from plants of the *Aglaonema* cultivar Camouflage in the following characteristics:

1. Leaves of plants of the new *Aglaonema* were broader and had more acuminate apices than leaves of plants of the cultivar Camouflage.
2. Plants of the new *Aglaonema* and the cultivar Camouflage differed in leaf coloration as plants of the cultivar Camouflage had tri-colored leaves with contrasting dark and mid-green chevrons on a light green background with random dark and mid-green spots and flecks and dark green-colored margins.

Plants of the new *Aglaonema* can also be compared to plants of the cultivar B. J. Freeman, disclosed in U.S. Plant Pat. No. 6,857. In side-by-side comparisons conducted in Chamrajpet, Bangalore, India, plants of the new *Aglaonema* differed from plants of the *Aglaonema* cultivar B. J. Freeman in the following characteristics:

1. Plants of the new *Aglaonema* were more outwardly arching than plants of the cultivar B. J. Freeman.
2. Plants of the new *Aglaonema* were more freely clumping than plants of the cultivar B. J. Freeman.
3. Plants of the new *Aglaonema* had smaller leaves than plants of the cultivar B. J. Freeman.
4. Plants of the new *Aglaonema* and the cultivar B. J. Freeman differed in leaf and leaf petiole coloration as plants of the cultivar B. J. Freeman had darker green-colored leaves and green-colored leaf petioles.
5. Plants of the new *Aglaonema* were more low temperature tolerant than plants of the cultivar B. J. Freeman.

BRIEF DESCRIPTION OF THE PHOTOGRAPH

The accompanying colored photograph illustrates the overall appearance of the new *Aglaonema,* showing the colors as true as it is reasonably possible to obtain in colored reproductions of this type. Colors in the photograph may differ slightly from the color values cited in the detailed botanical description which accurately describe the colors of the new *Aglaonema.* The photograph comprises a side perspective view of a typical plant of 'Calypso' grown in a container.

DETAILED BOTANICAL DESCRIPTION

The cultivar Calypso has not been observed under all possible environmental conditions. The phenotype may vary somewhat with variations in environment such as temperature and light intensity without, however, any variance in genotype.

The following observations and measurements describe plants of the new *Aglaonema* that were grown in 25-cm containers, in Homestead, Fla., in a polypropylene-covered shadehouse with light levels about 2,500 foot-candles. During the production of the plants, temperatures ranged from 2 to 43° C. Plants used for the photograph and description were about 14 months from planting. Color references are made to The Royal Horticultural Society Colour Chart, 1995 Edition, except where general terms of ordinary dictionary significance are used.

Botanical classification: *Aglaonema hybrida* cultivar Calypso.

Parentage:

*Female, or seed, parent.*—Proprietary selection of *Aglaonema hybrida* identified as code number KSG 86-28, not patented.

*Male, or pollen, parent.*—Unnamed selection of *Aglaonema tricolor* (Nicolson) Jervis, not patented.

Propagation:

*Type.*—By divisions.

*Time to initiate roots.*—Summer: About 18 to 20 days at 25 to 36° C. Winter: About 30 to 35 days at 15 to 28° C.

*Time to produce a rooted plant.*—Summer: About 30 to 35 days at 25 to 36° C. Winter: About 40 to 45 days at 15 to 28° C.

*Root description.*—Thick, fibrous, fleshy; off-white in color.

*Rooting habit.*—Freely-branching; dense.

Plant description:

*Plant form.*—Erect when young, becoming outwardly arching as leaves develop; inverted triangle, symmetrical and uniform.

*Vigor/growth rate.*—Vigorous; relatively rapid growth rate. Plant size appropriate for 25-cm containers.

*Growth habit.*—Freely clumping habit; plants typically produce above five to six offshoots per plant; full, dense and bushy appearance.

*Plant height.*—About 41 cm.

*Plant width (spread).*—About 57 cm.

*Stem description.*—Length: About 15 cm. Diameter: About 2.4 cm. Internode length: About 1.3 cm. Aspect: Upright. Strength: Good. Color: 147A with random spots, close to 144A.

*Foliage description.*—Appearance: Single; clasping. Length: About 26 cm. Width: About 11.5 cm. Shape: Oblong. Apex: Acuminate. Base: Obtuse. Margin: Entire. Orientation: Initially upright to roughly horizontal; twisting. Texture, upper and lower surfaces: Smooth, glabrous; thick, leathery; rugose. Veins: Recessed on upper surface and prominent on lower surface. Venation pattern: Pinnate. Color: Developing leaves, upper surface: 144A; chevrons, spots and splashes, close to 148C to 148D; venation, similar to lamina. Developing leaves, lower surface: Close to 147C; venation, close to 144D. Fully expanded leaves, upper surface: Ground color, darker green than 147A; chevrons, darker green than 194A; random spots and splashes, darker green than 194A or close to 150C; venation, similar to lamina. Fully expanded leaves, lower surface: Ground color, close to 147A; venation, along veins and random spots and splashes, close to 145D to close to 157C. Petiole: Aspect: Bent outwardly. Length: About 10.25 cm. Diameter, distal: About 2 cm. Diameter, proximal: About 6 mm. Wing length: About 8.4 cm. Wing diameter: About 7.5 mm. Color: Developing leaves, petiole and wing: Close to 144D. Fully expanded leaves, petiole: Close to 157C. Fully expanded leaves, wing: Close to 157C; random spots, close to 147A.

Inflorescence description: Inflorescence development has not been observed on plants of the new *Aglaonema* grown under shadehouse production conditions.

Disease/pest resistance: Plants of the new *Aglaonema* have been observed to be resistant to pathogens common to *Aglaonema* such as *Xanthomonas* and *Phytophthora.* Plants of the new *Aglaonema* have not been observed to be resistant to pests and other pathogens common to *Aglaonema*.

Weather tolerance: Plants of the new *Aglaonema* have been observed to be tolerant to wind, rain and temperatures ranging from 2 to 43° C.

It is claimed:

1. A new and distinct cultivar of *Aglaonema* plant named 'Calypso', as illustrated and described.

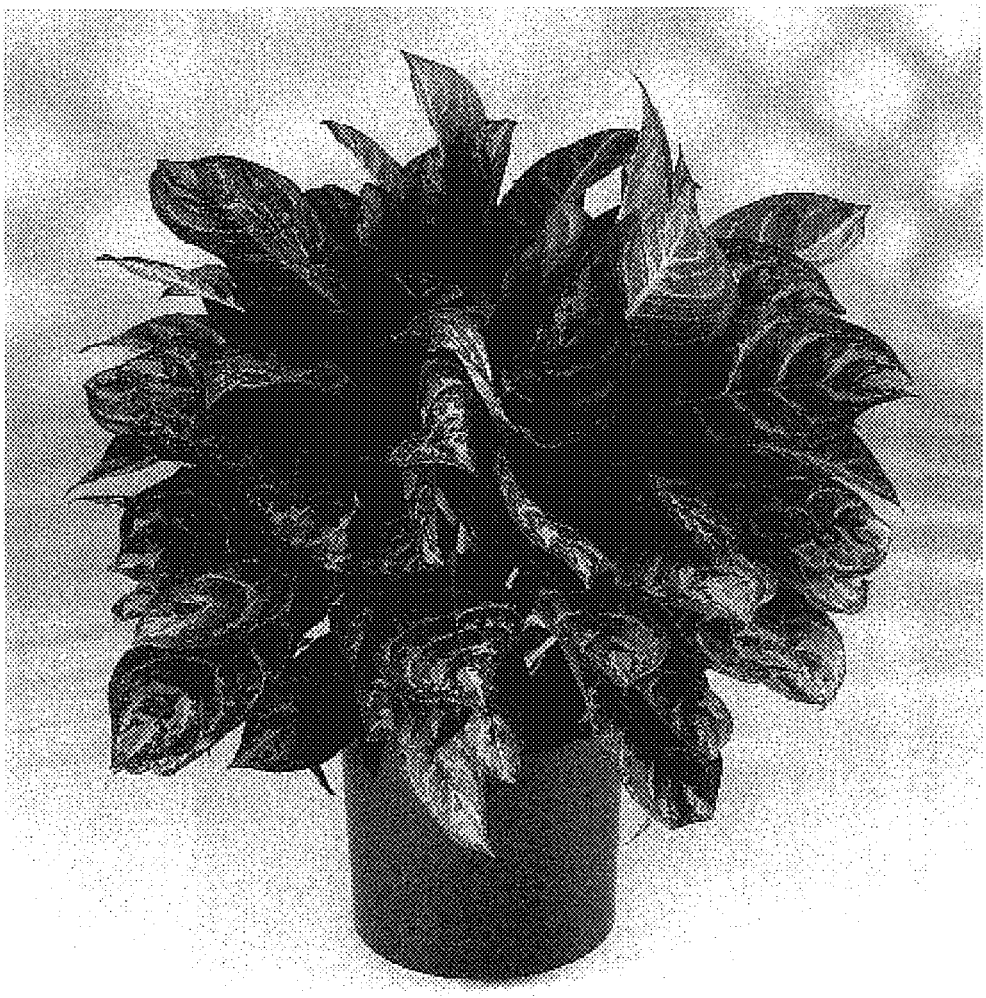

* * * * *